(12) United States Patent
Garcia-Ortiz et al.

(10) Patent No.: US 7,811,537 B2
(45) Date of Patent: *Oct. 12, 2010

(54) SYSTEMS AND METHODS FOR AIR PURIFICATIONS USING SUPERCRITICAL WATER OXIDATION

(75) Inventors: Asdrubal Garcia-Ortiz, Chesterfield, MO (US); Sunggyu Lee, Columbia, MO (US); John Wootton, St. Louis, MO (US)

(73) Assignee: DRS Sustainment Systems, Inc., St. Louis, MO (US)

(*) Notice: Subject to any disclaimer, the term of this patent is extended or adjusted under 35 U.S.C. 154(b) by 14 days.

This patent is subject to a terminal disclaimer.

(21) Appl. No.: 11/751,382

(22) Filed: May 21, 2007

(65) Prior Publication Data

US 2007/0217980 A1 Sep. 20, 2007

Related U.S. Application Data

(63) Continuation of application No. 10/971,391, filed on Oct. 22, 2004, now Pat. No. 7,722,823.

(51) Int. Cl.
*B01D 53/56* (2006.01)
(52) U.S. Cl. .................. 423/219; 95/156; 422/110; 422/168
(58) Field of Classification Search .......... 95/156; 423/219; 422/110, 112, 113, 120, 168
See application file for complete search history.

(56) References Cited

U.S. PATENT DOCUMENTS

| 4,013,560 A | * | 3/1977 | Pradt .................. 210/761 |
| 4,338,199 A | | 7/1982 | Modell |
| 4,539,303 A | | 9/1985 | MacLean et al. |
| 4,543,190 A | | 9/1985 | Modell |
| 5,080,692 A | | 1/1992 | Lee et al. |
| 5,106,513 A | | 4/1992 | Hong |
| 5,252,224 A | * | 10/1993 | Modell et al. .............. 210/695 |
| 5,386,055 A | | 1/1995 | Lee et al. |
| 5,516,952 A | | 5/1996 | Lee et al. |

(Continued)

FOREIGN PATENT DOCUMENTS

DE    102 14 165 A1    2/2004

OTHER PUBLICATIONS

Shaw, R.W., "Supercritical Water Oxidation of Toxic Military Materials: Current Status".

(Continued)

*Primary Examiner*—Stuart Hendrickson
*Assistant Examiner*—Richard M Rump
(74) *Attorney, Agent, or Firm*—Sonnenschein Nath & Rosenthal LLP

(57) ABSTRACT

Systems and methods using the properties of supercritical water to allow raw air including a contaminant to be combined with water and to be purified in a supercritical water oxidation (SCWO) process. A supercritical water oxidation (SCWO) air purifier will generally take in a mixture of water and raw air which includes oxygen via a pumping and mixing apparatus, put the mixture into a supercritical water reactor (SCWR), and run the resultant effluent stream through a system for separating the water from the resultant clean air and the other relatively harmless outputs of the supercritical water reactor (SCWO).

20 Claims, 6 Drawing Sheets

U.S. PATENT DOCUMENTS

| | | | |
|---|---|---|---|
| 5,571,423 A * | 11/1996 | Daman | 210/761 |
| 5,663,237 A | 9/1997 | Lee et al. | |
| 6,051,145 A | 4/2000 | Griffith et al. | |
| 6,103,129 A | 8/2000 | Bond et al. | |
| 6,264,844 B1 | 7/2001 | Modell et al. | |
| 6,340,722 B1 | 1/2002 | Lee et al. | |
| 6,511,601 B2 | 1/2003 | McMurtrey et al. | |
| 6,519,926 B2 | 2/2003 | Hazleback | |
| 6,585,890 B2 | 7/2003 | Li et al. | |
| 6,709,601 B2 | 3/2004 | Wofford, III et al. | |
| 6,709,602 B2 | 3/2004 | Spritzer et al. | |
| 2002/0113024 A1 | 8/2002 | Pilz et al. | |

OTHER PUBLICATIONS

Shaw, R.W. and Dahmen, N., "Destruction of Toxic Organic Materials Using Super-Critical Water Oxidation: Current State of the Technology," Supercritical Fluids—Fundamental and Applications, pp. 425-437, Kluwer Academic Publishers, Dordrecht, The Netherlands, 2000.

Gidner, A. and Stenmark, L., "Supercritical Water Oxidation of Sewage Sludge—State of the Art," Chematur Engineering AB.

U.S. Environmental Protection Agency, "EIMS Metadata Report—Document: Carbon Monoxide and the Nervous System," http://oaspub.epa.gov/eims/eimsapi.dispdetail?deid=64363, printed on Feb. 15, 2007.

Abeln, J., Kluth, M., Petrich, G., and Schmieder, H., "Supercritical Water Oxidation (SCWO): A process for the treatment of industrial waste effluents," http://www.turbosynthesis.com/summitresearch/bord-paperkorr.pdf, 2001.

Abeln, J. and Kluth, M., "Waste Oxidation in Supercritical Water Using a Transpiring Wall Reactor".

"Supercritical Water Oxidation State-Of-The-Art Environmental Technology," General Atomics and Affiliated Companies.

Spritzer, M., Elliott, J.P. and Hazlebeck, D.A., "Advanced Hydrothermal Oxidation of Shipboard Wastes".

Minett, S. and Fenwick, K., "Supercritical Water Oxidation for Organic Waste Disposal".

Supercritical Fluids Fundamentals and Applications, Chapters 1, 13, 14, 17, 19, 20, 22, Kluwer Academic Publishers, Dordrecht, The Netherlands, 2000.

Supercritical Fluids Molecular Interactions, Physical Properties, and New Applications, Chapters 1, 4, 5, and 6, Springer-Verlag, Germany 2002.

* cited by examiner

SYSTEMS AND METHODS FOR AIR PURIFICATIONS USING SUPERCRITICAL WATER OXIDATION

CROSS REFERENCE TO RELATED APPLICATIONS

This application claims priority to and is a Continuation of U.S. Utility patent application Ser. No. 10/971,391 filed Oct. 22, 2004, now U.S. Pat. No. 7,722,823. The entire disclosure of which is herein incorporated by reference.

BACKGROUND OF THE INVENTION

1. Field of the Invention

This disclosure relates to the field of air purification and converting air which is unsafe for human use into air which humans can safely breathe. In particular, this disclosure relates to the use of supercritical water oxidation to purify air.

2. Description of the Related Art

In recent years the need to segregate individuals from dangerous substances in the air has become one of increasing interest. All human beings must breathe and the introduction of airborne agents into the air they inhale creates a dangerous situation whereby individuals can be killed or injured and can strain medical response capability in an area. While all environmental air contains some impurities which can harm those breathing it, such as cold viruses and allergen molecules, modern warfare, terrorism, technology changes, and increasing globalization have led to an increased likelihood of larger scale contamination of air where sources of clean air can become quickly necessary to prevent catastrophic outcomes.

The danger of a chemical, biological, or nuclear weapon being unleashed on military forces, or on civilian centers, is a nightmare scenario for many government organizations. Such an attack can stymie military effectiveness or bring day to day economic activity to a grinding halt. Even without the purposeful use of nuclear, biological, or chemical weapons, the possibility of accidents involving these agents in populated areas is also a danger and governments must be able to respond to protect the citizenry. Still further, increases in globalization have led to increased danger of communicable disease. The recent Severe Acute Respiratory Syndrome (SARS) outbreak and fear of other dangerous natural contagions transmitted in the air has dramatically highlighted the need for clean air. In public forums such as stadiums, malls, convention centers, or airplanes where a large population is breathing the same air, it is desired to have air handling systems able to remove contaminants to prevent widespread exposure to a contagion. Further, in the event of a catastrophic incident, governments and emergency response agencies need to be able to quickly provide safe working conditions for health workers and other emergency responders to contain and destroy contaminants, whether natural or man-made, whenever and wherever may be necessary.

From the above, the need to provide safe air supplies may come upon a population suddenly, may be preferable but not necessarily required in anticipation of a potential release, or may be constant such as in hospitals or "clean rooms," where the need for cleaned air is always necessary as environmental air is simply too dirty for the specialized use to which the air is put. The need for decontamination may be known or predicted or an increased risk may be known to be likely in some situations. In other situations it may come without warning.

An airborne contaminant's danger level will generally depend on concentration. The concentration of a contaminant in the air being breathed will generally need to be above a particular threshold or else exposure is unlikely to cause concern. Most contaminants, if sufficiently dispersed, are not particularly dangerous. Therefore, protection against contamination usually requires the ability to either provide air which is known to be safe and has been stored for use during the contamination period, or to filter air which is contaminated to remove the contamination and provide safe air. The use of stored air is generally less effective as the storage requires specialized tanks and processes, and generally the amount of air which can be stored is relatively small. Instead, filtration is generally used, particularly if one is attempting to provide safe air to a group of individuals.

Filtration for harmful contaminants generally works by pulling some or all of the contaminant from the air into a solid filter. The resulting air is then provided to the users and generally only includes a reduced concentration of the contaminant such that the levels are sufficiently low that the contaminant is no longer harmful or, at the worst, no longer debilitating.

To prevent introduction of contaminants later, the clean air is generally pumped into an isolation environment which prevents introduction of unfiltered air and in which the individuals needing air are located. Smaller protective suits can provide an isolation environment for a single person while larger isolation structures can house multiple individuals. These isolation structures are, therefore, often the preferred method of providing safe air. Isolation structures can have economies of scale for filtration where larger more powerful air intake devices can be used to supply air to the structure. Further, a structure can allow individuals therein to perform tasks as they normally would instead of being forced to work in cumbersome individual protective suits.

Isolation structures may be permanent or may be temporary and may be used in any environment where safe air is needed. These environments may not be suitable for human occupancy because air is contaminated, or because air simply does not exist. In emergency responses or military field activities on the Earth, a temporary structure is generally preferred as it can be quickly setup anywhere when needed, and more easily stored when not needed. Often the temporary structure is inflatable whereby the structure can be setup in the zone of contamination and can then be filled with clean air using a portable filtration system to filter outside environmental air. The internal air pressure then provides the shape to the structure. Once inflated, the structure will be able to provide a safe haven for multiple people and a staging point for the use of contamination suits to venture further into a contaminated area. Further, the structure can often be provided with more efficient heating, cooling, or other environmental control units (ECUs) than individual protective suits can include.

FIGS. 1 and 2 provide for a first embodiment of an isolation shelter, in particular a collective protection shelter of the type commonly used by the United States military. This structure is intended to be vehicle portable (as shown in FIG. 2) and is usually transported on a High Mobility Multipurpose Wheeled Vehicle (HMMWV or Humvee) (70). Once deployed, as it is in FIG. 1. the shelter (75) will have been inflated and will comprise a self supporting isolation shelter. In the depicted embodiment, the shelter (75) comprises two structural "buildings" connected side-by-side. There is also an external airlock allowing access inside the shelter (75). The Humvee (70) is still attached to the shelter (75) and generally serves as a command and control center for the shelter (75) as well as a power source via its engine to run components in the shelter (75). In an embodiment, the collective protection shelter will also generally have an environmental control unit (ECU) (not shown) and may include an external generator.

Traditionally, on both portable filtration units and in permanent structures, filtration was performed by use of deep bed activated carbon filters or similar filters which block particles larger than a particular size and/or that react with particles of a particular type.

While this type of system is well understood, filters of this type all suffer from similar drawbacks In the first instance, changing the filter generally requires a potentially hazardous operation. As contaminants are captured by the filter to clean the air, the filter therefore will contain a high concentration of contaminants which will often make the filter quite toxic. These contaminants are generally still dangerous and biologically active within the filter material. Therefore, individuals handling the filter need to be careful that they are not accidentally exposed to the contaminants or that they do not inadvertently introduce the concentrated contaminants into an unfiltered air stream. In many respects, the filter cleans the air while creating a dangerous solid waste (namely the filter itself) which has to be safely disposed of to avoid later contamination. The contaminant is not eliminated by the filtration, it is simply concentrated and captured in a more easily disposable form.

Filters of the traditional type also have the problem of failing after a certain amount of time. As a filter is used, the ability of the filter to successfully filter out additional contaminants is often compromised and a dirty filter can reintroduce contaminants to the filtered air. Further, as filters become full of contaminants the air flow is often slowed so that motors drawing air into the structure must work harder or an insufficient amount of air is provided. As humans generate carbon dioxide while breathing, which is toxic to them, with insufficient clean air flow into the system, air can rapidly become dangerous even if outside contamination is successfully removed Filters are also part of the significant logistic trail in both military and civilian protection and can also be a significant expense. To date, there is no production system that incorporates a method to measure the absorbent capacity level remaining in filtration material. In the absence of this, protocol dictates that a filter be changed after a predetermined number of hours in service, irrespective of whether it has filtered contaminated air or not. This means that the filter is changed more frequently than may be needed when it is in use to prevent any unintended failure, Each change of filter requires personnel to leave the isolation environment and to change the filter As well as being a tedious and dangerous task, it offers the possibility that the new filter might not seat correctly, leaving the system potentially at risk and introducing the danger that personnel may be exposed to the contaminated air while outside the shelter.

One proposal to attempt to deal with the need to change filters is regenerative filtration whereby the filter can be remotely cleaned. There have been numerous different types of these proposed such as pressure swing, temperature swing, electronic swing and hybrid systems thereof. Regenerative filtration systems, while effective, are bulky and consume more power and, hence, are only useable in certain applications. Further, regenerative filters provide no energy recovery but actually use additional energy to operate as they must have power to clean. Further, the regenerative filter cannot provide aid to the other environmental control aspects of the ECU. The regenerative filter does not provide for heating or cooling of the air which must be provided by the ECU. This makes the regenerative filter an expensive alternative. Finally, a regenerative filter is still generally a standard filter, and while it can self-clean is generally subject to the limitations on air flow and contaminant capture as a more traditional filter.

SUMMARY

Because of these and other problems in the art, described herein are systems and methods for using supercritical water oxidation to purify air. These systems and methods are generally designed to be portable and to allow for relatively high speed purifying of air.

Described herein, in an embodiment, is a method for generating breathable air comprising: having a supercritical water reactor (SCWR); providing said SCWR with water and raw air; said raw air comprising oxygen and at least one organic contaminant; placing said water in a supercritical state thereby dissolving said contaminant into said water; allowing said oxygen in said raw air to completely oxidize said contaminant creating an effluent stream comprising oxygen, water and oxidation outputs; removing said effluent stream from said supercritical state; separating said water from said oxidation outputs and said oxygen; and providing said oxidation outputs and said oxygen as breathable air.

In an embodiment of the method, in said step of separating, a concentration of at least one of said oxidation outputs is determined and said concentration is altered prior to said step of providing.

In an embodiment of the method said raw air is air drawn from Earth's atmosphere and may further comprise nitrogen. In another embodiment, said outputs of oxidation include at least one of: hydrogen, carbon dioxide, and carbon monoxide.

In another embodiment of the method, in said step of allowing; said oxidation creates additional water, and said additional water is also removed in said step of separating from other oxidation outputs and said water provided in said step of providing may be said water removed in said step of removing from a prior occurrence of said method.

In another embodiment of the method, thermal or work energy is recovered from said effluent stream for use in said step of placing. The pressure and temperature levels of said effluent stream may also manipulated to result in the heating or cooling of said breathable air, In another embodiment of the method, said raw air further comprises an inorganic contaminant which may be precipitated from said effluent stream, In another embodiment, there is described herein, a system for purifying air comprising: raw air comprising oxygen, nitrogen, and at least one organic contaminant; water; means for taking said water and said raw air and increasing pressure and temperature to make said water supercritical; said supercriticality and the presence of said oxygen in said raw air forming said organic contaminant into at least one decomposition product, said water, oxygen, nitrogen, and at least one decomposition product comprising an effluent stream; and means for separating said water from said effluent stream; wherein at least one of said at least one decomposition product is selected from the group consisting of: hydrogen, carbon dioxide, carbon monoxide.

In another embodiment of the system, there may be included means for recovery of thermal energy from said effluent stream, means for recovery of work energy from said effluent stream, or means for reducing the temperature and pressure of said air stream to about 294K and about 1 atm, respectively.

In a still further embodiment, there is described, a system for purifying air comprising: feeds for raw air and input water; a supercritical water reactor (SCWR); a condenser; a heat exchanger; a pressure exchanger; and a pressure regulator; wherein, said input water and raw air are provided to said SCWR by said feeds; wherein, said input water, when in said SCWR, is in a supercritical state; wherein, in said SCWR, a contaminant is removed from said raw air forming clean air; wherein, said SCWR releases said clean air and output water as an effluent stream; wherein said heat exchanger removes thermal energy from the said effluent stream for use in raising the temperature of said input water and raw air; wherein said pressure exchanger removes work energy from the said effluent stream for use in raising the pressure level of said input water and raw air; wherein said pressure regulator adjusts the pressure level of said clean air to a particular pressure level according to its temperature level; and wherein, said condenser can separate said output water from said clean air

DESCRIPTION OF PREFERRED EMBODIMENT(S)

Figure 1:
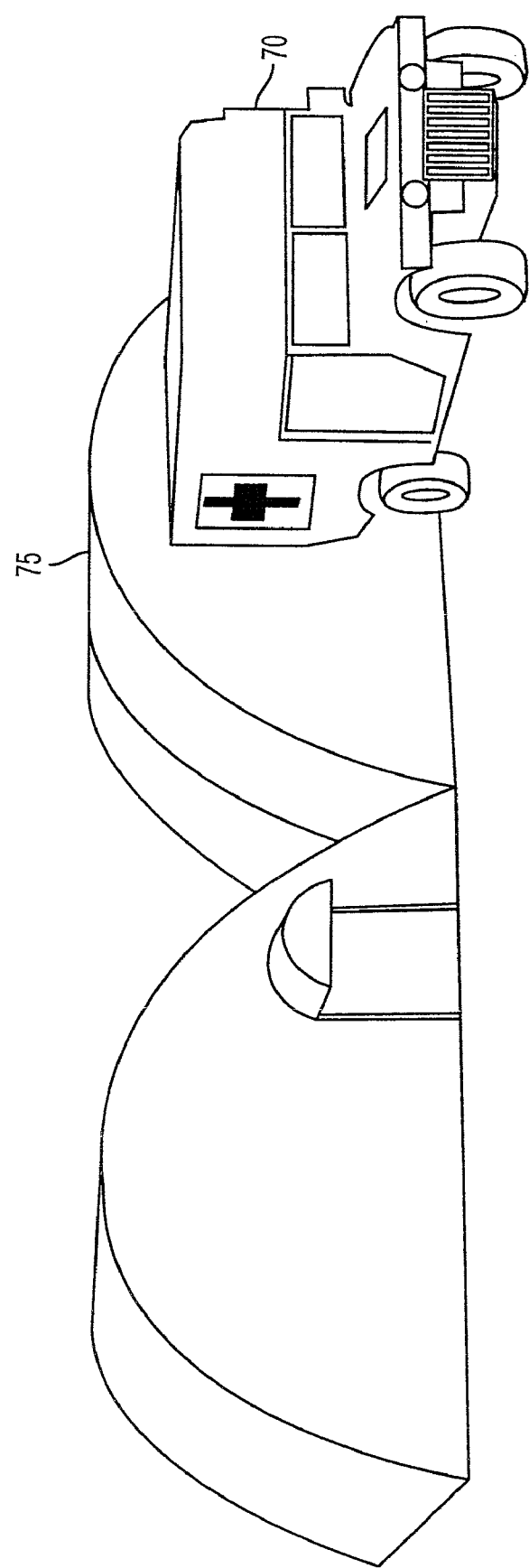
FIG. 1 Provides a drawing of an embodiment of a collective protection shelter deployed from a High Mobility Multipurpose Wheeled Vehicle (HMMWV or Humvee).

Disclosed herein, among other things, is a supercritical water oxidation (SCWO) system for converting raw air which may or may not contain any kind of contaminant, whether or not harmful to human beings or whether or not present in sufficient quantities to harm human beings, into clean air which may be safely breathed by humans. The raw air may be supplied from any source of air but will generally be from atmospheric air available to the system.

The term "raw air" as used herein is intended to be a general term relating to the gaseous material generally recognized as air whose purification is desired. This will generally be because the raw air is viewed as not clean and contains a contaminant to be removed. However, the raw air is desired to be processed, even if such cleaning is unnecessary. Raw air generally will comprise air of the type generally available in Earth's atmosphere regardless of exact chemical composition and will usually include molecules of nitrogen and oxygen. Air will also generally comprise a small percentage of other gases, such as, but not limited to, carbon dioxide, and water vapor. The air may further comprise any number of contaminants which will generally be solid particulates suspended in the air or particular gases.

A contaminant, as used herein, is essentially any material mixed with, suspended by, or in solution with the air in a sufficient concentration that breathing of the contaminated air can result in harm to human beings and specifically includes, but is not limited to, pollutants, microorganisms, biologicals, chemicals, particulates or other materials. One of ordinary skill in the art would recognize that some of these contaminants are not necessarily harmful. However, contaminants will have little to no positive effect to the human body and could result in harm, even if the risk and harm is small. Most contaminants of interest will be organic contaminants of the type forming chemical or biological warfare agents (CBWAs) but that is not strictly required, and either or both organic and inorganic contaminants can be included.

Generally, it will be presumed that the materials to be removed are either biological or chemical in nature such as microorganisms, pollens, or other materials which have been placed in atmospheric air. It will be recognized that the contaminants in cases where the filtration systems discussed below are most likely to be used have been purposefully introduced by man for the purpose of terrorism or as a weapon however, environmental contaminants such as pollen, dander, or natural microorganisms, may also qualify as contaminants. Contaminants may be present in relatively small quantities over a relatively large area yet still cause wide-spread contamination. The SCWO air purifier (50) will generally be presumed to be used in conjunction with an isolation shelter, in particular a Collective Protection Shelter as used by the U.S. Military. While this disclosure will focus on such systems in conjunction with a Chemically and Biologically Protected Shelter System (CBPSS), it would be recognized that any isolation shelter may be used, whether temporary or permanent and including, but not limited to: Chemically Protected Deployable Medical Systems (CP DEPMEDS), Chemically Hardened Air Transportable Hospitals (CHATH), Simplified Protection Equipment (SCPE), or Joint Transportable Collective Protection Systems (JTCOPS).

To begin discussion on the removal of contaminants, it is useful to begin with an understanding of supercritical water which is used in the purification process.

Figure 3:
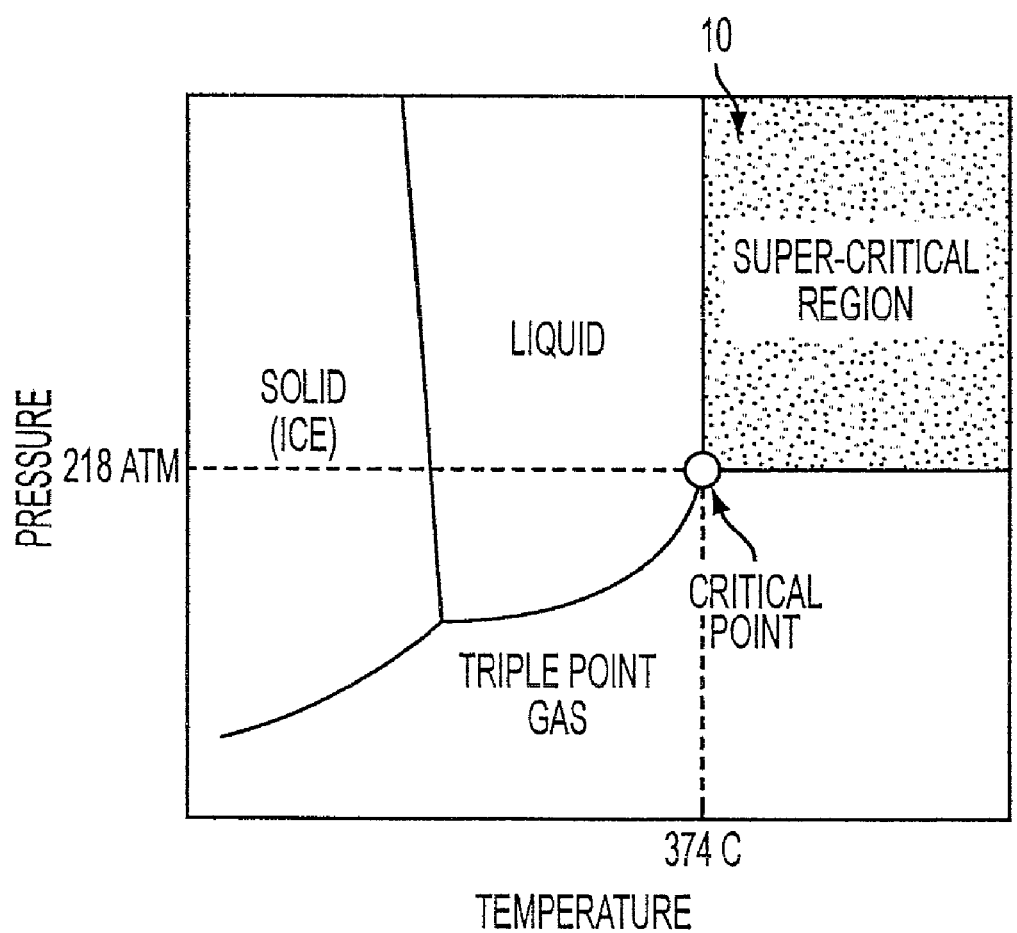
FIG. 3 Provides a graph showing the conditions of supercritical water.

FIG. 3 generally shows the region (10) where water exists in its supercritical state. Supercritical water is recognized as having a very high solubility for organic materials, and a very low solubility of inorganic materials. Supercritical water is used to separate out both organic and inorganic contaminants from the raw air and then provide for clean air from the process.

FIG. 4 provides an embodiment of a block diagram showing the layout of a supercritical water oxidation (SCWO) air purifier (50) which can be used to purify raw air into breathable air by using SCWO processes. In FIG. 4 there are generally three broad component stages which relate to the operation of the SCWO air purifier (50).

In the stage one components (100) raw air (515) and water (415) are input into the system, placed under pressure and heated In the stage two components (200), a supercritical water reactor (SCWR) (201) takes in the pressurized and heated water and raw air mixture (615) and uses the water (415) as a solvent and the oxygen in the raw air (515) as an oxidant to remove and/or destroy the contaminants from the raw air (515). In the stage three components (300), the water (415) is condensed and collected and the effluent air (315) is shuttled to the target destination. As part of the stage three components, the effluent air (315) may be cooled using properties of the pressurized air. Each of these component stages will now be discussed in more detail.

In the stage one components (100) there are two chemical feeds representing the two inputs raw air feed (101) and input water feed (103). The raw air feed (101) is generally arranged so as to allow raw air (515) to be obtained from a pressurized air tank (102) from prior pumping of atmospheric air into the tank. The raw air feed (101) generally includes a compressor (112) to compress the raw air (515) to place it under pressure. The compressor (112) preferably pressurizes the raw air (515) to a pressure level near the critical pressure of water (218 atm) shown in FIG. 3. The compressor (112) may increase the pressure using any system of method known now or later developed The raw air (515) will also generally pass through a preheater (107) which heats the raw air (515) to a point near the critical temperature of water (374° C.) as also shown in FIG. 3. The raw air in this case will generally be environmental air from the Earth's atmosphere outside of the isolation environment. The amount of air fed by air feed (101) is controlled by a flow controller (115) which will serve to insure that the correct amount of raw air (515) is supplied to the SCWR (201) to prevent air from passing through SCWR (201) without proper purification. The amount of raw air (515) fed into the SCWR (201) will generally depend on the organic content ("purity") of the raw air, and, in an embodiment, is determined during operation by the gas analysis taking place near the end of the process stream in air tester (307). At a minimum, however, the amount of raw air (515) processed will need to be sufficient to meet the make-up air flow required to ensure breathable air. Further, in a CBPSS, other inflatable isolation structure, or many other isolation structures, the air flow will generally need to be sufficient to maintain positive pressure inside the isolation structure. The raw air (515) fed by raw air feed (101) will generally comprise a mixture of gases including nitrogen, oxygen and a relatively small percentage of various other gases which are not contaminants as well as at least one contaminant to be removed Generally, the nitrogen will comprise about 78% of the mixture, oxygen about 21% of the mixture and the other materials comprising about 1% of the mixture in accordance with the composition generally accepted as Earth's atmospheric air. For the purpose of this disclosure, the exact composition of the gases prior to purification is not important. Instead, the purpose of the system is to produce outputs which can be combined into breathable air. In particular, the oxygen concentration is of particular importance as is the level of carbon dioxide. Pursuant to Occupational Safety and Hazard Administration (OSHA) regulations, breathable air should include at least 19.5% oxygen and no more than 1% carbon dioxide. For purposes of this disclosure, effluent ("clean" or "breathable") air (315) will therefore preferably have constituents in this range, however, any air which can be breathed by a human for some period of time without injury is classified as clean or breathable air. In an alternative embodiment, pure nitrogen gas or other inert gases may also be provided on an additional feed (105) to be used to purge the system.

The input water feed (103) includes a high pressure pump (104) and a booster pump (106) designed to feed input water (415) into the SCWO air purifier (50) using any type of liquid feed technology known now or later developed. The pump (104) preferably pressurizes the water (415) to a pressure level near the critical pressure of water (218 atm) shown in FIG. 3. Before the input water (415) is provided to the SCWR (201), it will generally pass through a preheater (107) which heats the water to a point near the critical temperature (374° C.) also shown in FIG. 3. The raw air (515) and water (415) may be mixed prior to entering SCWR (201) as in the depicted embodiment forming an input raw air/water mixture (615) or may be mixed in the SCWR (201) in an alternative embodiment. Generally, there will be valves (111) at various points between the air feed (101), water feed (103), and the SCWR (201) (and at other points in the SCWO air purifier (50)) to prevent back feed, to regulate the amount of each material provided in the raw air/water mixture (615), and to maintain the pressure inside the SCWR (201).

As mentioned above, the first stage components (100) may also include a purging system. The purge system will generally comprise a nitrogen or other inert gas feed (105) which may provide inert gas into the system under pressure This purge can be used to clean the system of residual materials during system shutdown or to clear out potentially dangerous air, contaminants, or other items which could get into the isolation environment.

Input water (415), in the embodiment of FIG. 4 comprises the water (415) output from the condenser (305) (as discussed later) which is re-fed into the system. The input raw air/water mixture (615) may pass through the energy recovery system obtaining heat or pressure from the effluent stream (215) prior to insertion into the SCWR (201). In an alternative embodiment, the water (415) separated from the effluent stream (215) may simply be allowed to retain heat and/or pressure and be directly cycled back as input water (415) Heat may also be transferred to the raw air/water mixture (615) as a by-product from internal combustion processes or other engines or drivers which are operating the pump (104) or other components of the SCWR air purifier (50). These exchangers (503) and (505) may utilize any methods or means known to those of ordinary skill in the art to exchange heat and pressure from the effluent stream (215) to the input water/air mixture (615) to help raise the pressure and temperature levels of the input mixture (615). In this way, the heat and pressure of the effluent stream (215) is recycled back into the input stream (615) which helps to make the system run more efficiently and require that less heat be generated by the heating elements (223) or preheater (107), or less work be produced by pumps (104) and (106).

The recycling of heat and pressure and their use in the SCWO air purifier (50) is also discussed later in conjunction with providing for cooling of the effluent air (315) to provide for efficient air conditioning when the system is used in hot environments. This however, occurs during the third stage components (300) and is discussed therein.

Figure 4:
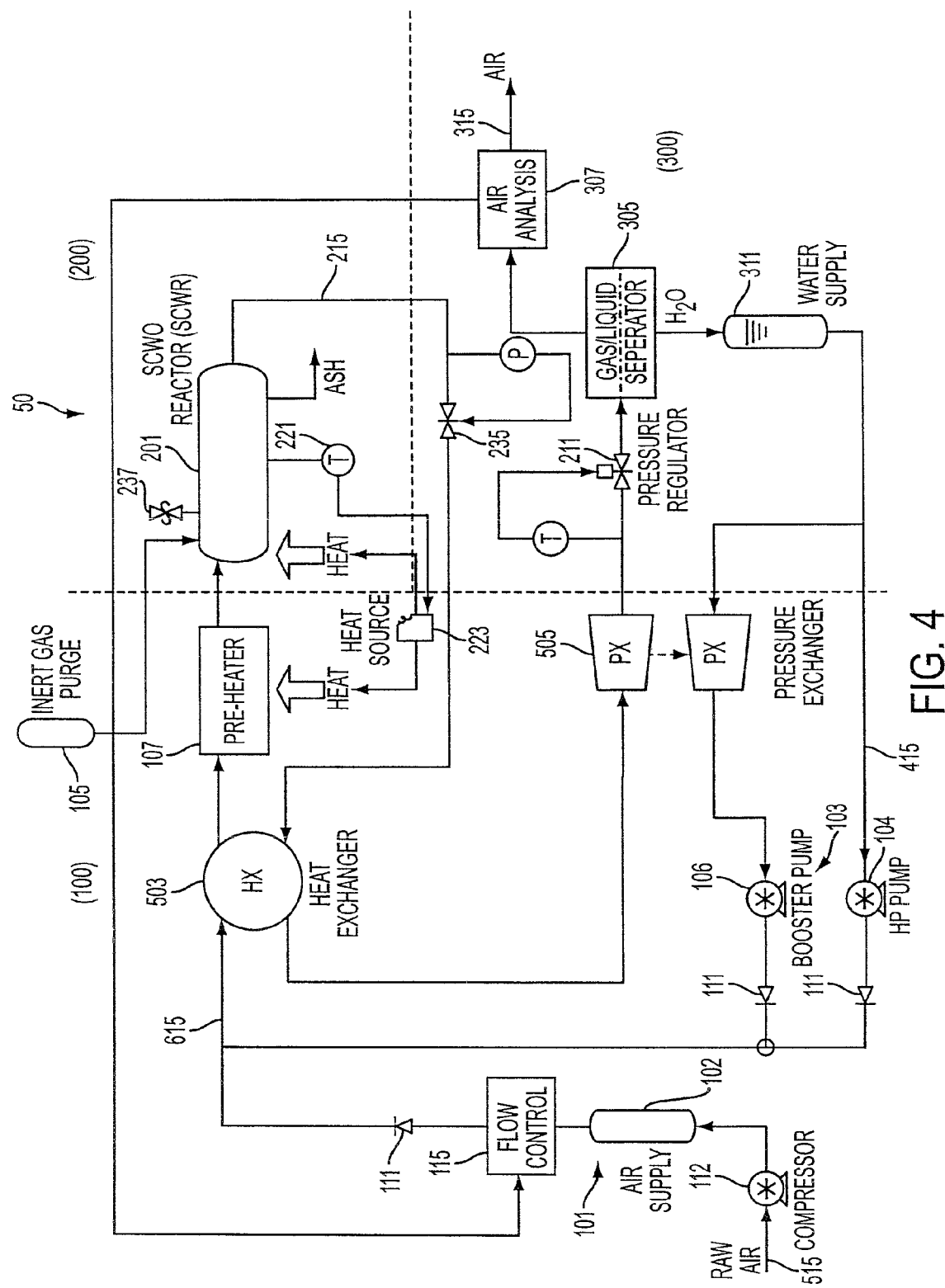
FIG. 4 Provides a general block diagram of an embodiment of an SCWO air purification system.

Returning to the walk through of FIG. 4, as the input mixture (615) of water (415) and raw air (515) enters the second stage components (200) it enters into the SCWR (201). The SCWR (201) is typically a vessel constructed according to known high pressure design codes for Hastelloy-C276, Inconel, or other suitable material. In an alternative embodiment, the reactor may be constructed of stainless steel. The SCWR (201) may be either a mixing-type or continuous tubular type As depicted in FIG. 4, the SCWR (201) may be equipped to obtain additional heat from a heat source (223) which heats the input water/air mixture. This includes the pre-heater (107) as well as additional heating elements (223) in the SCWR (201). Alternatively, heat exchange components may be included in the system as discussed above.

In the SCWR (201), the supercritical water drives an oxidation reaction to break down the organic contaminants present in the raw air into their decomposition products such as hydrogen, water, carbon dioxide ($CO_2$) or carbon monoxide (CO). In particular, the supercritical water completely dissolves all organic materials likely to be present in the raw air. All these ingredients further will generally react completely with the oxygen in the raw air in a homogeneous reaction phase within the SCWR (201) resulting in creation of their decomposition products.

Unlike many other treatment processes, the process converts organic species into water, hydrogen, carbon monoxide, carbon dioxide and other decomposition products as opposed to simple filtration capture of the contaminant. The decomposition products of organics are all generally harmless so long as not provided in too high of a concentration. As oxygen in the raw air is used up by the reaction and carbon dioxide is created, there is a very slight possibility that the resultant air produced might not be breathable.

The amount of oxygen used, however, is generally very minimal (as the contaminants are generally a very small percentage of the raw air (515)). Therefore, it is highly unlikely that sufficient oxygen would be used up to render the air unbreathable. Further, generally only a relatively small amount of carbon dioxide is created. If concentrations of organics are sufficiently high to prove problematic, however, oxygen concentration in an embodiment is increased by removing other materials through the use of air scrubbers as is understood in the art. Alternatively, the air intake may be increased to provide more air flow If carbon dioxide concentration is a concern, $CO_2$ scrubbers are added to the effluent stream in an embodiment as discussed later. Inorganic compounds, which are generally insoluble in the supercritical water can be precipitated out as ash or salt from the SCWR. These can then be removed. A solid particulate can be removed using any type of system known now or later discovered.

In the depicted embodiment, the SCWR (201) is monitored by a temperature controller (221) which senses the internal temperature of the SCWR (201) and as necessary applies additional heat input to the SCWR (201) using heating elements (223) to maintain the temperature in the SCWR (201) near the critical temperature of water. The pressure inside the SCWR (201) is preferably monitored by a back pressure regulator (235) to maintain the pressure in the SCWR (201) near the critical pressure of water. A pressure relief valve (237) may also be present in case the pressure inside the SCWR (201) reaches dangerous levels. If such high levels are detected, pressure will generally be released from SCWR (201) via a vent to prevent danger from explosion or similar risks.

Once the SCWR (201) has purified the air, the resultant effluent stream (215) which will include the clean air (315) as well as the input water (415) (which will also be very clean as a byproduct of the reaction) is passed through a forward pressure regulating valve (211) and into the stage three components (300). Valve (211) generally serves to control the pressure of the effluent stream entering condenser (305).

The stage three components (300) are principally related to separating water (415) and effluent air (315) in the effluent stream (215) in a useful manner. Some or all of the water (415) may be removed depending on the desired effluent air (315). In particular, some water (415) may purposefully not be separated to provide more humid air to eliminate dryness for occupants. Water (415) which is separated out will generally be stored in a storage vessel (311) until needed and then re-fed into the SCWR (201) by the water feed (103). However, in an alternative embodiment, the water (415) may be drained off to form a potable water source due to the cleaning of the water which occurs in the SCWR (201) simultaneous to cleaning of the raw air (515). In an embodiment, raw water in need of processing is fed into the SCWR (201) along with the raw air (515). The SCWR (201) then cleans both air and water simultaneously. This embodiment provides for a powerful single system for both processes. The cleaning of water using SCWO is discussed in additional detail in U.S. patent application Ser. No. 10/840,716, the entire disclosure of which is herein incorporated by reference.

The pressure and temperature in the stage 3 components (300) will generally be lowered to allow precipitation of the water (415) out of its supercritical state. This pressure and temperature lowering may also be used to lower the temperature of the air to a comfortable "room temperature" without need for traditional air conditioning setups. The precipitation of water (415) will generally be performed by a condenser (305). The resultant liquid water is collected in the storage vessel (311) while the remaining oxygen and nitrogen gas (and other gases and suspended particles, if present) will be sent to an air tester (307). The air tester (307) may include devices for altering the output air (such as scrubbers to remove excess carbon dioxide or carbon monoxide) as well as devices for evaluating whether or not the output air still contains any harmful contaminants. Presuming the air is determined to be clean, and the percentage of various components is also not toxic, the effluent air (315) will generally be piped into the isolation environment as clean breathable air. If there is a problem with the effluent air (315), the effluent air (315) may be cycled back through the SCWR (201), exhausted outside the isolation environment, or scrubbed to place the effluent air (315) in desired form.

Figure 2:
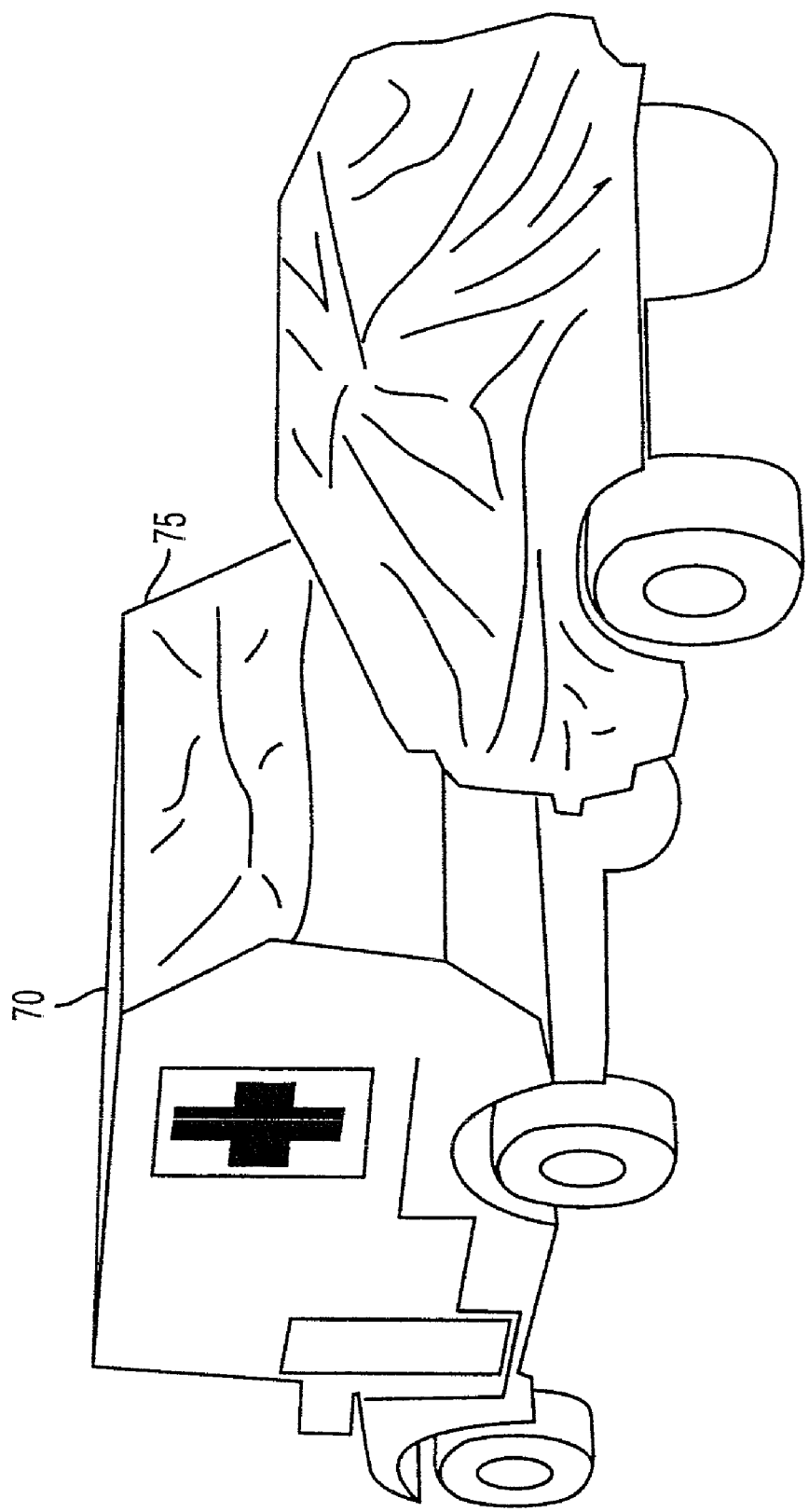
FIG. 2 Shows the collective protection shelter of FIG. 1 stored on board a Humvee.

Control of the SCWO air purifier (50) is performed in the embodiment of FIG. 2 by monitoring the SCWR (201) effluent air stream (315) with the air tester (307). The air tester (307) will generally include a gas chromatograph or other suitable sensor to determine the composition in effluent stream (215). From these results, a user can adjust the air feed (101) and water feed (103) to control the residence time of the raw air/water mixture in the SCWR (201). The air tester (307) may control air fed into the SCWR (201) by means of the mass flow controller (115) using automatic control, Alternatively, the system may be entirely regulated by a user.

As the effluent air (315) is being provided to the user, the effluent air (315) will obviously need to be reduced from the supercritical pressure and temperature of water which it was at in the SCWR (201) to a comfortable temperature to prevent injury from the heat. This return can provide for an additional benefit of allowing temperature manipulation of the air without resort to traditional air conditioning type systems. In particular, the expansion of the air from the approximately 218 atm of pressure at the supercritical state to 2 or 1 atm which is the logical pressure that the air would be provided is a reversible adiabatic (isentropic) process. This pressure decrease can be carried out by pressure transfer to the input raw air/water mixture. Further, the clean air will generally automatically decrease in pressure as it is ejected into the isolation shelter as the isolation shelter will generally be pressured at slightly above 1 atm. Simple calculation of the pressure drop from 218 atm to 1 atm indicates that the air will in fact be placed at a temperature significantly below freezing if just being exhausted from the SCWR (201) to the isolation shelter and would be much too cold to be provided to a human user.

Figure 5:
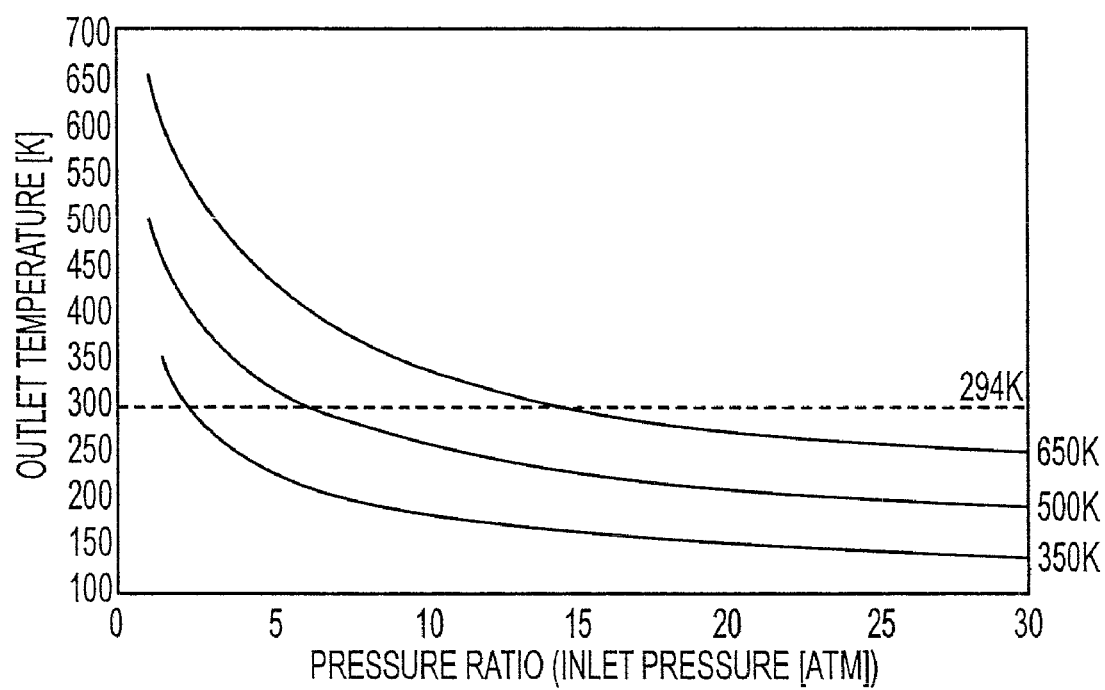
FIG. 5 Provides a graph showing various adiabatic process lines for various inlet temperatures and pressures.

To control this temperature decrease to provide for useful cooling, without freezing, it is preferable to utilize a relationship as shown in FIG. 5. FIG. 5 provides an indication of the temperature at which the effluent air (315) would end up in the shelter and somewhere downstream over various air exhaust pressures for three different air exhaust temperatures (the temperature that the air would be exhausted into the shelter). As can be seen, if the desired shelter temperature is selected as 294 K or about 70 degrees Fahrenheit at 1 atm of pressure, levels of air exhaust temperature and pressure for the air can be selected to obtain that result as shown by the dashed line.

Figure 6:
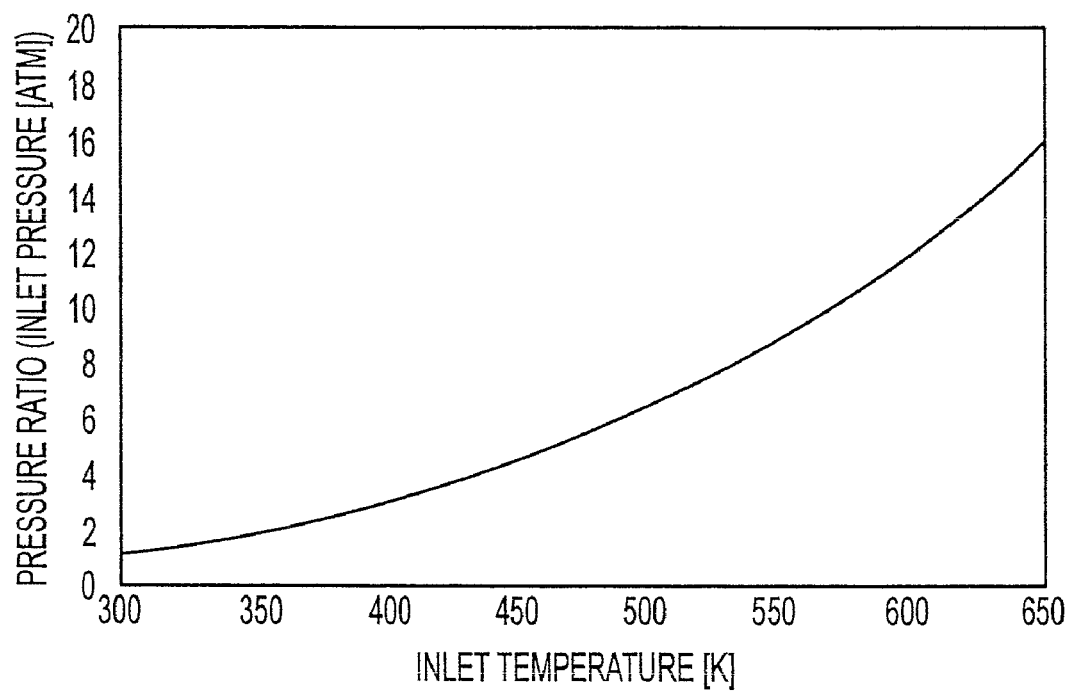
FIG. 6 Provides a graph showing inlet pressure and temperature ratios that yield a 294 K outlet temperature.

The indications of this graph can then be displayed as the graph of FIG. 6. This graph provides that for the fixed room temperature (about 70 degrees Fahrenheit) selected, there is a curve of air exhaust temperature(s) and pressures required to reach the desired room temperature at about 1 atm pressure. The system can then utilize pressure and heat exchange (energy recovery) as discussed in conjunction with the stage one components (100) above to place the effluent stream (215) at a desired pressure and temperature combination upon exhaust of the effluent air (315) into the shelter. Using this information, the effluent air (315) will reach the desired temperature in the isolation shelter as it naturally adjusts to about 1 atm of pressure. In particular, at any point of this line, if the effluent air (315) is exhausted into the isolation shelter, at that pressure and temperature, the effluent air (315) will reduce to a comfortable temperature in the isolation shelter as its pressure naturally adjusts to about 1 atm. Noticing that any point on the line of FIG. 6 will result in effluent air (315) at 1 atm being the desired temperature, generally a lower point on the line (lower temperature and pressure combination) will be chosen, in this way, most of the heat and pressure from the effluent air (315) may be removed through the heat and pressure exchangers (503) and (505) respectively allowing for recycling of these components in the system and improved efficiency. Once the desired point of exhaust temperature and pressure is reached (generally on or near the curve of FIG. 6), the effluent air (315) is ejected and, given its prior state, will reduce to about one atmosphere of pressure (the pressure it is at in the ambient environment). As the effluent air (315) adjusts to this pressure, its temperature will continue to fall to the target temperature allowing for the system to provide air at the target temperature. If this air is used in a self contained structure, it should be clear that the structure will therefore have air of a comfortable temperature even if air outside the structure is not a comfortable temperature.

The embodiment of FIG. 4 does not require a particularly large setup, or particularly complicated operation. It should be apparent that the SCWO air purifier (50) could be assembled to be readily vehicle portable to a variety of locations. In particular, the SCWO air purifier (50) would preferably be able to fit on a pallet such as a forklift pallet or a 463L pallet as used by the United States Air Force. Alternatively, a scaled up version of the SCWO air purifier (50) could be placed in an over-the-road (OTR) truck trailer or on a pallet, crop, or flatrack utilized by Load Handling System (LHS) trucks such as the HEMTT-LHS truck used by the United States Army. Likewise, a sealed-down version could be used for protecting the occupants inside a vehicle.

There is generally no need to provide additional water to allow the reaction once a particular amount of water has been provided, and the water will cycle in an endless loop through the system. In an alternative embodiment as previously discussed, the supercritical air purification technology may be combined with a supercritical water purifier such as that discussed in U.S. patent application Ser. No. 10/840,716, the entire disclosure of which is herein incorporated by reference. In this embodiment, both raw air (515) and raw water may be provided to the system together providing both clean air and clean water as outputs. The percentage of each may be selected based on how much of each is needed as output (with excess being discarded or simply serving as a surplus), or to maximize the efficiency of the reaction. Regardless of which method is used, in the SCWR (201) whether the contaminant was originally waterborne or airborne is irrelevant. The contaminant will be destroyed in the SCWR (201). Therefore both clean water and clean air will be able to be removed from the system. Depending on which of these products are to be used, one of these may be recycled or vented or both may be sent to final end users.

SCWO air purifiers (50) can be used in a wide variety of applications and for a wide variety of purification tasks. One such use is clearly military use. Soldiers in the field may be exposed to numerous foreign agents including foreign germs. Further, many countries are known to have arsenals of nuclear, chemical, or biological weapons which create dangerous air borne contaminants. Soldiers operating in these environments can be provided with collective protection shelters in which to take refuge in the event that such a germ or other agent is present. This can help the soldiers to weather an attack utilizing these weapons, and can also help to speed recovery from such agents and to minimize downtime from naturally occurring contaminants.

In an alternative embodiment, while the above presumes that the air inside the isolation shelter is clean and environmental air is contaminated, it should be apparent that the system can work in the reversed configuration. In particular, the system can also be used for isolation of contaminated (and generally contagious) individuals. For instance, a dangerous germ agent with which some soldiers become infected may be prevented from additional airborne contamination by placing those soldiers into a quarantine ward. The air in this ward can be purified using an SCWO air purifier (50) prior to returning the air to the ambient, or to providing the air to another shelter. Because the SCWR not only kills the germ, but will actually reduce it to decomposition products completely destroying its structure, the germ has little chance of causing further problems outside the isolation structure and is very effectively eliminated.

The system also has clear indications for clean rooms such as in hospitals or in manufacturing facilities which require clean air to prevent damage to delicate manufactured components and which can require isolation and quarantine. In these systems, organic components will be broken down into readily identifiable gases which, if they present a problem, can be scrubbed from the air by well known systems. Generally, these gases will not provide a problem as they will not interact with the components so can remain in the air. Further, inorganic materials such as dust can be removed as ash utilizing separation systems in the SCWR and providing only gases to the facility. This can make the facility simpler to utilize for those inside as well as actually improving cleanliness by not simply filtering potentially dangerous or destructive agents, but by actually destroying or separating them.

While the invention has been disclosed in connection with certain preferred embodiments, this should not be taken as a limitation to all of the provided details. Modifications and variations of the described embodiments may be made without departing from the spirit and scope of the invention, and other embodiments should be understood to be encompassed in the present disclosure as would be understood by those of ordinary skill in the art.

The invention claimed is:

1. A method for cleaning air prior to input to an enclosure, the method comprising:
   providing a supercritical water reactor (SCWR);
   providing an air flow control device;
   providing an air analysis device;
   receiving raw air from outside the enclosure via said air flow control device, said raw air comprising oxygen and at least one organic contaminant;
   providing said raw air, via said air flow control device, to said SCWR;
   providing input water to said SCWR;
   placing said water in a supercritical state thereby dissolving said contaminant into said water;
   allowing said oxygen in said raw air to oxidize said contaminant creating an effluent stream comprising remaining oxygen from said raw air, water and oxidation outputs;
   removing said effluent stream from said supercritical state;
   separating said water from said oxidation outputs and said oxygen;
   determining the composition of said oxidation outputs via said air analysis device;

adjusting the amount of said raw air provided to said SCWR by the air flow control device based on the determined composition of said oxidation outputs such that said remaining oxygen is at or above a predetermined level; and providing, via said air analysis device, said oxidation outputs and said remaining oxygen as output air to within the enclosure.

2. The method of claim 1 wherein in said step of, determining composition of said oxidation outputs, a concentration of at least one of said oxidation outputs is determined and said concentration is altered prior to said step of providing said oxidation outputs and said oxygen as output air.

3. The method of claim 1 wherein said raw air is air drawn from Earth's atmosphere.

4. The method of claim 1 wherein said raw air further comprises nitrogen.

5. The method of claim 1 wherein said outputs of oxidation include at least one of: hydrogen, carbon dioxide, or carbon monoxide.

6. The method of claim 1 wherein said outputs of oxidation includes carbon monoxide.

7. The method of claim 6 further comprising: removing said carbon monoxide from said oxidation outputs prior to said providing said oxidation outputs and said oxygen as output air.

8. The method of claim 1 wherein in said step of allowing; said oxidation creates additional water, and said additional water is also removed in said step of separating from other oxidation outputs.

9. The method of claim 1 wherein said water provided in said step of providing is said water removed in said step of removing from a prior occurrence of said method.

10. The method of claim 1 wherein thermal energy is recovered from said effluent stream for use in said step of placing.

11. The method of claim 1 wherein work energy is recovered from said effluent stream for use in said step of placing.

12. The method of claim 1 wherein the pressure and temperature levels of said effluent stream are manipulated to result in the heating or cooling of said output air.

13. The method of claim 1 wherein said raw air further comprises an inorganic contaminant.

14. The method of claim 13 wherein said step of allowing said inorganic contaminant is precipitated from said effluent stream.

15. A system for cleaning air prior to input to an enclosure, the system comprising:

an air flow control device operatively configured to receive raw air drawn from outside the enclosure, said raw air comprising oxygen, nitrogen, and at least one organic contaminant;

an input water feed;

means for taking water from said input water feed and said raw air from said air flow control device and increasing pressure and temperature to make said water supercritical; said supercriticality and the presence of said oxygen in said raw air forming said organic contaminant into at least one decomposition product, said water, remaining oxygen from said raw air, nitrogen, and at least one decomposition product comprising an effluent stream;

means for separating said water from said effluent stream to define an effluent air stream, wherein at least one of said at least one decomposition product in said effluent air stream is selected from the group consisting of: hydrogen, carbon dioxide, and carbon monoxide; and an air analysis device operatively configured to determine a composition of said effluent air stream, wherein the air flow control device adjusts the amount of said raw air received by said air flow control device based on the determined composition of said effluent air such that said remaining oxygen is at or above a predetermined level and further configured to output said effluent air stream having said remaining oxygen to within the enclosure.

16. The system of claim 15 further comprising: means for recovery of thermal energy from said effluent stream.

17. The system of claim 15 further comprising: means for recovery of work energy from said effluent stream.

18. The system of claim 15 further comprising: means for reducing the temperature and pressure of said air stream to about 294K and about 1 atm, respectively.

19. The method of claims 1, wherein the predetermined level of remaining oxygen is 19.5%.

20. The system of claim 15 wherein the predetermined level of remaining oxygen is 19.5%.

* * * * *